United States Patent [19]
Midha et al.

[11] Patent Number: 6,127,385
[45] Date of Patent: Oct. 3, 2000

[54] METHOD OF TREATING DEPRESSION USING L-THREO-METHYLPHENIDATE

[75] Inventors: Kamal K. Midha, Hamilton, Bermuda; Martin Teicher, Waltham, Mass.; Vijai Kumar, Morris Plains, N.J.

[73] Assignee: Pharmaquest Limited, Hamilton, Bermuda

[21] Appl. No.: 09/262,385

[22] Filed: Mar. 4, 1999

[51] Int. Cl.$^7$ .................................................. A61K 31/445
[52] U.S. Cl. ........................................... 514/317; 514/315
[58] Field of Search ...................................... 514/315, 317

[56] References Cited

U.S. PATENT DOCUMENTS

| | | |
|---|---|---|
| 2,507,631 | 5/1950 | Hartman et al. . |
| 2,838,519 | 6/1958 | Rometsch . |
| 2,957,880 | 10/1960 | Rometsch . |
| 5,733,756 | 3/1998 | Zeitlin et al. . |
| 5,837,284 | 11/1998 | Mehta et al. . |
| 5,874,090 | 2/1999 | Baker et al. . |
| 5,908,850 | 6/1999 | Zeitlin et al. . |
| 5,922,736 | 7/1999 | Dariani et al. . |
| 5,936,091 | 8/1999 | Khetani et al. . |

FOREIGN PATENT DOCUMENTS

| | | |
|---|---|---|
| 1453828 | 10/1976 | United Kingdom . |
| 97 03671 | 2/1997 | WIPO . |
| 97 03672 | 2/1997 | WIPO . |
| 97 03673 | 2/1997 | WIPO . |
| 98 23263 | 6/1998 | WIPO . |
| 98 25902 | 6/1998 | WIPO . |
| 99 16 439 | 4/1999 | WIPO . |

OTHER PUBLICATIONS

Junkman et al Psychiat. Res. 78 (12): 115–118, Mar. 20, 1998.

Ding et al Psychopharmacology (Borlin) 131(1): 71–78, 1997.

Ding J. Labelled Compo. Radiopharm 34(10): 989–997, 1994.

Gatley et al. Life Sci. 58(12): 231–239, 1996.

Aoyama et al Pharm. Res 11(3): 407–411, 1994.

Hubbard et al J. Pharm. Sci 78 (11): 944–947, 1987.

Eckerman et al Pharmacol. Biochem. Behav. 40(4): 875–880, 1991.

Patrick et al J. Pharm. Exp. Ther. 241111:152158, 1987.

Srinivas Int J Pharm Exp Ther 241 300–306, 1987.

N.R. Srinivas, J.W. Hubbard, D. Quinn and K.K. Midha, Clin. Pharmacol. Therap. 52, 561–568, 1992.

N.R. Srinivas, J.W. Hubbard, E.D. Korchinski and K.K. Midha, Pharm. Res. 10, 14–21, 1993.

Y.S. Ding, J.S. Fowler, S.L. Dewey, G.J. Wang, J. Logan, S.J. Gatley and N. Pappas, Psychopharm. 131, 71–78, 1997.

S.L. Satel and J.C. Nelson, J. Clin. Psychiat, 50, 241–249, 1989.

R.J. Chiarello and J.O. Cole, Arch. Gen. Psychiat. 44, 286–295, 1987.

R.E. Emptage and T.P. Semla, Annals of Pharmacotherapy 30, 151–157, 1996.

A.E. Wallace, L.L. Kofoed and A.N. West, Am. J. Psychiat. 152, 929–931, 1995.

N.D. Volkow, G.J.Wang, J.S.Fowler, S.J. Gatley, J.Logan, Y.S.Ding, R.Hitzeman and N.Pappas, Amer. J. Psychiat. 155, 1325–1331, 1998.

*Primary Examiner*—Shep K. Rose
*Attorney, Agent, or Firm*—Herbert Dubno; Jonathan Myers

[57] ABSTRACT

A method of treating depression to elicit prompt relief from depression is disclosed. The method comprises the step of administering orally or non-orally to said patient, a therapeutically effective amount of l-threo-methylphenidate or a pharmaceutically acceptable salt thereof.

16 Claims, 4 Drawing Sheets

FIG.2 COMPOSITE SCORES FOR VIGOR

FIG. 3  COMPOSITE SCORES FOR DYSPHORIA

METHOD OF TREATING DEPRESSION USING L-THREO-METHYLPHENIDATE

FIELD OF THE INVENTION

This invention relates to a method of treating depression in a patient by oral or non-oral administration of 2S,2'S-methyl 2-phenyl-2-(2'-piperidyl)acetate, commonly known as 1-threo-methylphenidate, hereinafter referred to as 1-MPH and to pharmaceutical compositions containing 1-MPH designed to deliver 1-MPH to the central nervous system. More particularly the method of treatment is designed to provide relief to a depressed patient who is awaiting the onset of the antidepressive action of an antidepressant such as a selective serotonin re-uptake inhibitor, or any other class of antidepressant that requires administration over 2 to 6 weeks to demonstrate therapeutic effect.

BACKGROUND OF THE INVENTION

Orally administered racemic dl-threo-methylphenidate (dl-MPH) is widely used in the treatment of Attention-Deficit Hyperactivity Disorder (ADHD) in children and adults and also in the treatment of depression in patients suffering from cancer or AIDS, compulsive shopping disorder, narcolepsy, and hypersomnia. It is known that the therapeutic effect of dl-MPH in the treatment of ADHD in children is attributable to d-MPH (Srinivas et al, Clin. Pharmacol. Therap. 52, 561 to 568, 1992). Until recently, however, little was known about the potential pharmacological and/or therapeutic roles of 1-MPH because concentrations of 1-MPH in plasma and brain are very low due to extensive enantioselective first pass metabolism of 1-MPH after oral administration of dl-MPH (Srinivas et al, Pharm. Res. 10, 14 to 21, 1993). After intravenous administration of dl-MPH, however, both enantiomers of threo-methylphenidate are taken up into the brain although their patterns of distribution are different (Ding et al, Psychopharmacology 131, 71 to 78, 1997).

The use of oral stimulants such as dextroamphetamine or dl-MPH in the treatment of severe depressive disorders in the elderly or terminally ill depressed patients has been the subject of many studies over the years. After reviewing 85 publications on the subject, Satel and Nelson (J. Clin. Psychiat. 50, 241 to 249, 1989) were critical of the fact that many of the studies reported were methodologically unsophisticated and/or uncontrolled. They concluded that while stimulants are no more effective than a placebo in the treatment of primary depression, stimulants may be of value in the treatment of refractory patients and medically ill patients. Similarly, Chiarello and Cole (Arch. Gen. Psychiat. 44, 276 to 285, 1997) reviewed 81 publications and concluded that many of the older studies are inadequate although there was some evidence to support the use of psychostimulants in selected clinical instances. Emptage and Smith (Annals of Pharmacotherapy, 30, 151 to 157, 1996) reviewed 43 studies published from 1986 to 1995 and concluded that oral -MPH appears to be a safe and effective treatment for depressed, medically ill, elderly patients to provoke a rapid onset of antidepressant activity. Recently Wallace and co-workers (Am. J. Psychiat. 152, 929 to 931, 1995) conducted what they termed the first placebo-controlled double blind trial to demonstrate the efficacy of oral dl-MPH in older, medically ill depressed patients. The benefit of oral dl-MPH was statistically and clinically significant despite the small number of patients in the study (n=16). Depressive symptoms decreased markedly in 7 subjects (Hamilton depression scale decreased by >55%), moderately in a further 3 subjects (Hamilton depression scale decreased by 30 to 55%), minimally in 3 subjects (Hamilton depression scale decreased by <30%) and three patients were dropped from the study.

OBJECTS OF THE INVENTION

It is an objective of the invention to provide a method of treating a depressed patient to provide immediate relief from intense dysphoria by administering to the patient via an oral or non-oral route, a therapeutically effective amount of 1-MPH which refers herein to the base or hydrochloride salt or any other pharmaceutically acceptable salts thereof.

A further objective of the invention is to provide a method of treating a depressed mammal and particularly a depressed human patient with repeated doses of 1-MPH, either in immediate release form or sustained release form to provide relief while the patient awaits the onset of action of a conventional antidepressant drug.

A further objective of the invention to provide a test to ascertain how responsive a patient may be to certain forms of antidepressant therapy by administering 1-MPH orally or non-orally to the patient, observing the patient's response to the 1-MHP and utilizing that information to predict how effectively such a patient would be expected to respond to treatment with conventional anti-depressants which take 2 to 6 weeks to become optimally effective.

SUMMARY OF THE INVENTION

According to this invention, 1-MPH and/or its salts is a valuable rapidly acting anti-depressant and/or anti-dysphoric when administered by a route that avoids first pass metabolism. It may be used according to the present invention to treat a patient suffering from depression by administering to the patient, in an oral or non-oral form, a clinically effective dose of 1-MPH. The 1-MPH may either be in the form of its free base or in the form of a pharmaceutically acceptable salt, such as the hydrochloride salt, the acetate salt, the maleate salt or any other pharmaceutically acceptable acid addition salt.

The oral routes of administration that avoid the first pass metabolism are preferably sub-lingual administration or via the buccal mucosae.

The 1-MPH used according to the present invention has an enantiomeric purity of at least 95% and therefore contains no more than 5% d-MPH; the latter enantiomer may potentially be abused. Preferably the 1-MPH is enantiomerically pure.

The 1-MPH may be used to provide rapid antidepressant action for the relief of severe depression in, for example terminal cancer patients, patients with AIDS depression, or in severely depressed patients with suicidal ideation. The 1-MPH may also be useful as a diagnostic tool to identify severely depressed patients who are responders to serotonin re-uptake inhibitors (SSRLs). Examples of these SSRLs include fluoxetine hydrochloride, venlafaxine hydrochloride, paroxetine hydrochloride, nefazodone hydrochloride, and sertraline hydrochloride.

The drug is particularly useful in the treatment of severely depressed hospitalized patients and in depressed suicidal patients to provide immediate relief from their intense dysphoria. The drug may be given repeatedly, either as an immediate release or as a sustained release formulation to provide relief while the patient awaits the onset of conventional antidepressants which typically take 3 to 6 weeks to become effective. These conventional antidepressants can include serotonin re-uptake inhibitors (SSRLs) which have been discussed hereinabove as well as any other pharmaceutical composition that is recognized as safe and effective in the treatment of depression. Such other pharmaceutical compositions include atypical antidepressants which are antidepressant compounds with a chemical structure unrelated to selective serotonin reuptake inhibitors, tricyclics, tetracyclics, or monoamine oxidase inhibitors. Examples of such compounds are nefazodone and buprorion. Such other pharmaceutical compositions also include tricyclic antidepressants such as amitriptyline, imipramine, doxepin, maprotiline, protriptyline, nortriptyline, desimipramine, clomipramine, trimipramine or any other conventional tricyclic antidepressant.

The 1-MPH may be used to help severely depressed patients to recover a sufficiently euthymic mood to restore in them feelings of hope and a renewed will to live.

Another feature of the present invention is a diagnostic test which includes the 1-MPH in a method to determine how responsive a patient may be to certain forms of antidepressant therapy. Patients who respond dramatically to non-orally administered 1-MPH are patients with diminished serotonin transmission and a strongly lateralized serotonin system. Positive response to 1-MPH would indicate treatment with a drug such as a selective serotonin re-uptake inhibitor (SSRL) that would enhance serotonin transmission. While SSRLs are effective in many patients, some 30% of depression patients do not respond and less than half respond completely. Thus a positive response to 1-MPH is a valuable indicator that the patient is an SSRL responder and that it is worth persisting with an SSRL during the weeks that it takes for this class of drugs to be effective in treating depression.

The 1-MPH may be administered by one or more oral or non-oral routes of administration. Routes of administration include rectal administration in the form of liquids or suppositories, as well as a number of alternative routes of administration, including absorption through the nasal mucosae or the buccal mucosae, or the sub-lingual mucosae, various means of percutaneous administration by, for example, use of a transdermal patch, or by subcutaneous, intravenous, intramuscular, and intraperitoneal injection.

The daily dosage of the 1-MPH administered to a patient suffering from depression is 5 to 500 mg, preferably 25 to 250 mg/day and more preferably 25 to 125 mg/day.

The 1-MPH can be isolated from the racemic mixture of dl-MPH by preparative chiral high performance liquid chromatography (HPLC). In this procedure a non-polar octadecasilane HPLC column (25.4 mm×250 mm) is used in combination with a mobile phase (dichloromethane/acetonitrile) containing a chiral discriminator, namely α-10-camphorsulfonic acid, and a competing base, namely triethylamine. See Lim et al, 1985.

Example of Dosage Forms Transdermal Patch

The application of medicinal substances to the skin is an effective route of delivery of many drugs to the systemic circulation. The skin often has been referred to as the largest of the body organs; an average adult's skin has a surface area of about $2m^2$. Its accessibility and the opportunity it affords to maintain applied preparations intact for a prolonged time have resulted in its increasing use as a route of drug administration, whether for local, regional or systemic effects. Drugs are applied to the skin to elicit one or more of four general effects: an effect on the skin surface, an effect within the stratum corneum, a more deep-seated effect requiring penetration into the epidermis and dermis or a systemic effect resulting from delivery of sufficient drug through the epidermis and the dermis to the vasculature to produce therapeautic system concentrations.

Generally the drug is suspended/dispersed in a vehicle such as propylene glycol/isopropyl myristate. Other additives used are p-aminobenzoic acid or benzyl peroxide. The drug release from its vehicle is a function of concentration, solubility in the vehicle and the partition coefficient between the vehicle and the receptor site. Percutaneous absorption of the drug is enhanced by the use of occlusive techniques or by the use of penetration enhancers. Penetration Enhancers such as polyols e.g. glycerin, have a direct effect on the permeability of the skin. They act by increasing the thermodynamic activity of the penetrant, thereby increasing the effective escaping tendency and concentration gradient of the diffusing drug.

Generally the formulation for the patch is composed of two/three layers. Proceeding from the outer surface to the film in contact with the skin, these layers are a soft flexible backing of translucent polyethylene film, a drug containing film composed of acrylate adhesive matrix or ethylene-vinyl acetate and a protective liner composed of polyester film.

For 1-MPH, solvents such as various alcohols, dimethyl sulfoxide or decylmethyl sulfoxide may be utilized, and anionic surfactants such as sodium lauryl sulfate or various cationic, amphoteric or non-ionic surfactants may be appropriate.

Sublingual Tablets

Sublingual tablets are designed to dissolve very rapidly. Examples of such formulations include ergotamine tartrate, isosorbide dinitrate, isoproterenol HCl. The formulation of these tablets contain, in addition to the drug, a limited number of soluble excipients, usually lactose and powdered sucrose, but occasionally dextrose and mannitol. The process of making sublingual tablets involves moistening the blended powder components with an alcohol-water solvent system containing approximately 60% alcohol and 40% water.

In addition to 1-MPH, the prototype formulation for sublingual tablets may contain a binder such as povidone or HPMC, diluents such as lactose, mannitol, starch or cellulose, a disinegrant such as pregelatinized or modified starch, lubricants such as magnesium stearate, stearic acid or hydrogenated vegetable oil, a sweetener such as saccharin or sucrose and suitable flavoring and coloring agents.

Intranasal Formulation

For many years, the nasal delivery was used primarily for local action on the nasal mucosae. Despite its use in systemic delivery of desmopressin and vasopressin, its use as an alternate route for poorly absorbed oral drugs seems to have been ignored until recently. By virtue of relatively rapid drug absorption, possible bypassing of presystemic clearance, and relative ease of administration, delivery of drugs by nasal route offers an attractive alternative for administering systemically active drugs.

The prototype formulation for nasal solutions will contain 1-MPH dissolved in a suitable aqueous or non-aqueous solvent such as propylene glycol, an antioxidant such as ascorbic acid and aromatic oils as flavoring agents. The formulation may also contain suitable propellant(s).

Suppositories

The use of suppositories dates back to writings of the early Egyptians, Greeks and Romans. However it is only recently efforts are being carried out to correlate in vitro results with in vivo studies. The rectal suppositories for adults are usually tapered at one or both ends and weigh about 2 g each. The return is about 150 mm in length and contains a small amount of fluid of low buffering capacity with a pH of about 7.2. The suppository base such as cocoa butter is immiscible with aqueous tissue fluids but melts at body temperature.

In the prototype formulation for suppositories, the drug (1-MPH) is typically dissolved in a base such as cocoa butter, polyethylene glycol or glycerinated gelatin. The suppository mixture is poured and cooled in individual molds formed from plastic or foil and the excess is trimmed off and units are sealed and cut into desired packaging. The suppositories with low-melting ingredients are best stored in a cool place. Cocoa oil suppositories should be refrigerated.

Injectable Formulations

For intravenous or subcutaneous injection, a suitable 1-MPH acid salt will be supplied as sterile powder or crystals in sealed ampoules or vials. The formulation may be reconstituted in a sterile intravenous preparation such as normal saline, dextrose or water for injection. Alternatively, the intravenous formulation may be supplied as sterile aqueous solution of a suitable acid salt of 1-MPH in a sterile intravenous preparation such as normal saline, dextrose or water for injection.

For intramuscular administration, an acid salt of 1-MPH may be formulated as a sterile aqueous solution as described above, or alternatively, 1-MPH base may be dissolved in a suitable oil such as cotton seed oil or sesame oil.

Psychopharmacological Testing

Figure 1:
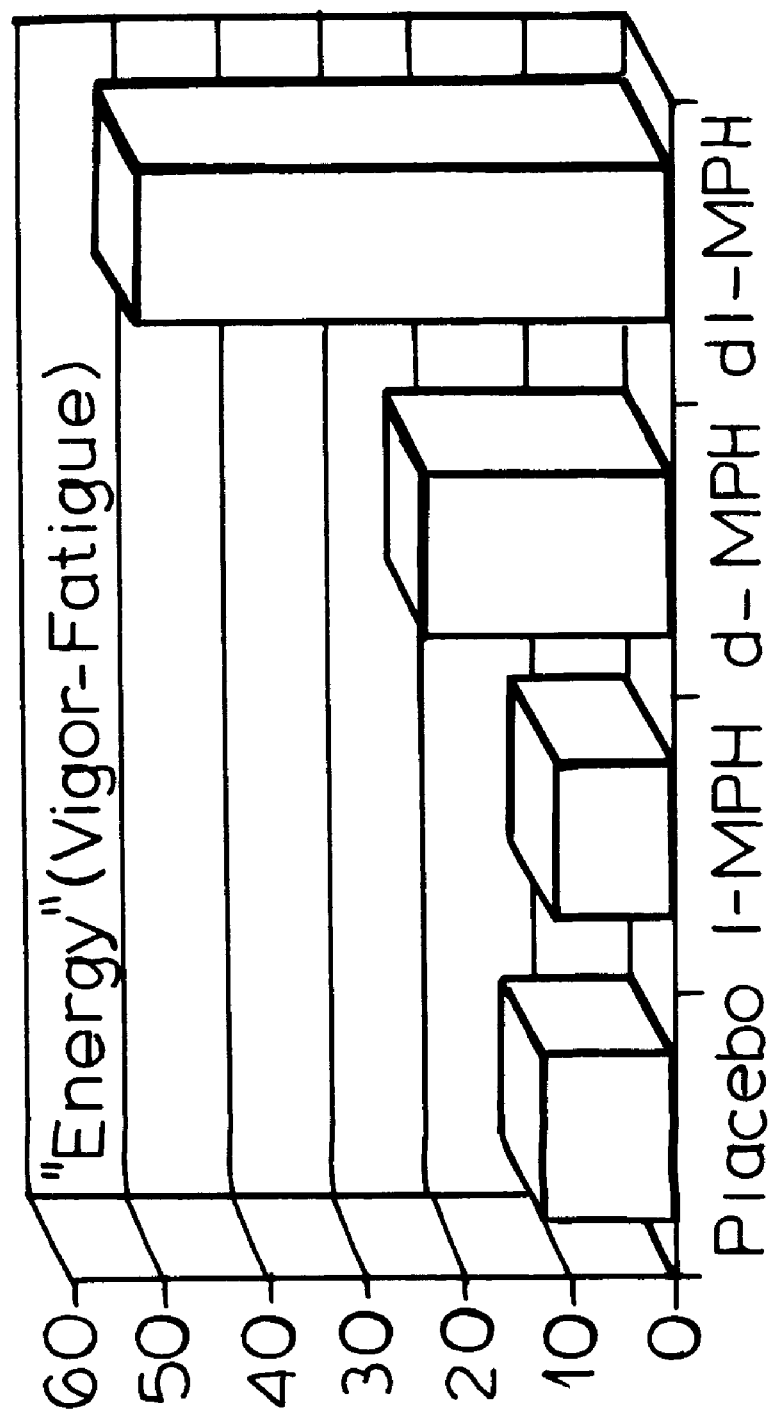
FIG. 1 is a series of 4 bar graphs showing the effect of intravenous administration of dl-MPH, d-MPH, 1-MPH and a placebo on the level of psychic energy of healthy patients who received each of these substances.

A balanced, randomized 4-phase cross-over study was carried out in 12 healthy male volunteers who each received intravenous administrations of dl-MPH, d-threo-methylphenidate (d-MPH), 1-MPH and placebo. The Profile of Mood State (POMS) rating scale was used to estimate pharmacodynamic factors including Anger-Hostility, Confusion-Bewilderment, Depression-Dejection, Fatigue-Inertia, Tension-Anxiety, and Vigor-Activity. In addition composite scores were also produced for "Energy" ("Vigor-Activity" minus "Fatigue-Inertia") and "Dysphoria" ("Anger-Hostility" plus "Depression-Rejection" plus "Tension-Anxiety"). See FIG. 1 which shows composite scores for "Energy" (Vigor minus Fatigue).

The results showed an overall effect of the drugs on "Energy". dl-MPH enhanced "Energy" is expected. "Energy" scores for the racemate were significantly different (paired t-tests) from those for 1-MPH and placebo. Surprisingly, however, d-MPH was not strongly energizing and did not differ significantly from the placebo or 1-MPH. See FIG. 1 and Table 1.

| ENERGY | PLACEBO | 1-MPH | d-MPH |
|---|---|---|---|
| 1-MPH | NS | — | |
| d-MPH | NS | NS | — |
| dl-MPH | 0.05 | 0.05 | 0.09 |

This paradox apparently arose because d-MPH enhanced both components of "Energy" (Vigor-Activity and Fatigue-Inertia) over the test period.

Figure 2:
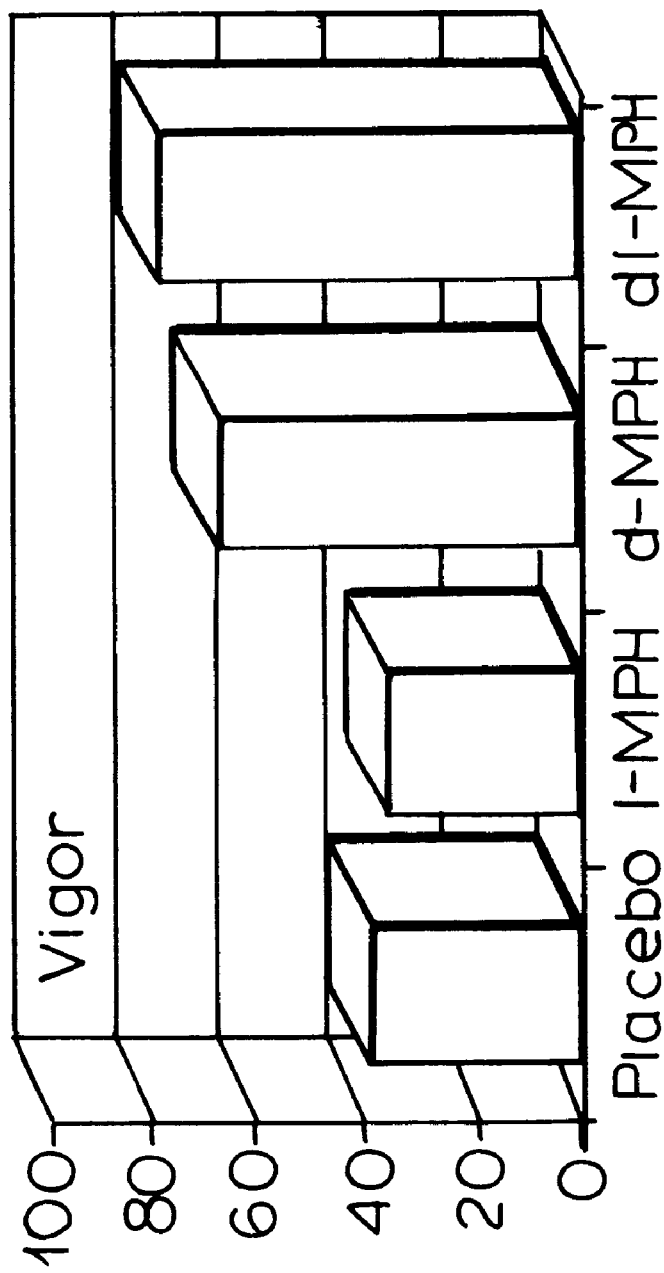
FIG. 2 is a series of 4 bar graphs showing the effect of intravenous administration of dl-MPH, d-MPH, 1-MPH and a placebo on the level of vigor of healthy patients who received each of these substances.

The vigor ratings for d- and dl-MPH were significantly different from those for 1-MPH and placebo. See FIG. 2. The Fatigue-Inertia factor was not a simple rebound phenomenon. There was some suppression in Fatigue ratings during the period when d-MPH was most activating, but Fatigue-Inertia scores did not rise above the initial basal level. The POMS rating for Fatigue-Inertia after d-MPH were significantly different from those after 1-MPH.

Figure 3:
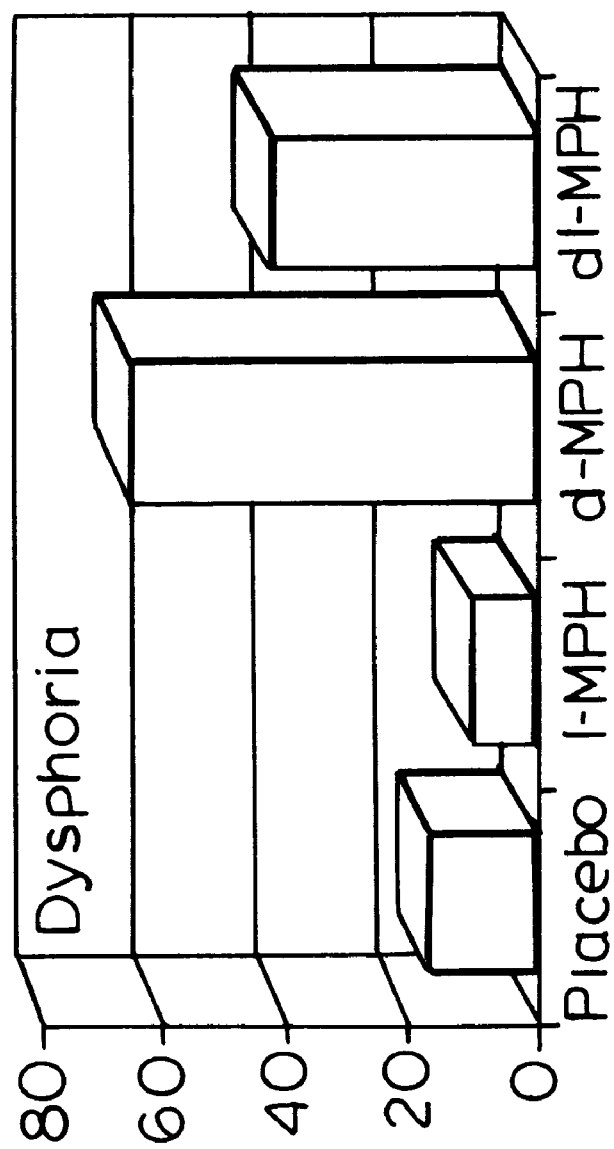
FIG. 3 is a series of 4 bar graphs showing the effect of intravenous administration of dl-MPH, d-MPH, 1-MPH and a placebo on the level of dysphoria of healthy patients who received each of these substances.

There were very robust effects of drug condition on composite "Dysphoria" ratings. The d-MPH and to a lesser extent dl-MPH both increased "Dysphoria" compared with the placebo or 1-MPH. See FIG. 3. The "Dysphoria Ratings" were numerically lower for 1-MPH than for the placebo. The effect was more marked when analysis included only 9 out of 12 subjects who showed some degree of "Dysphoria" on placebo.

Figure 4:
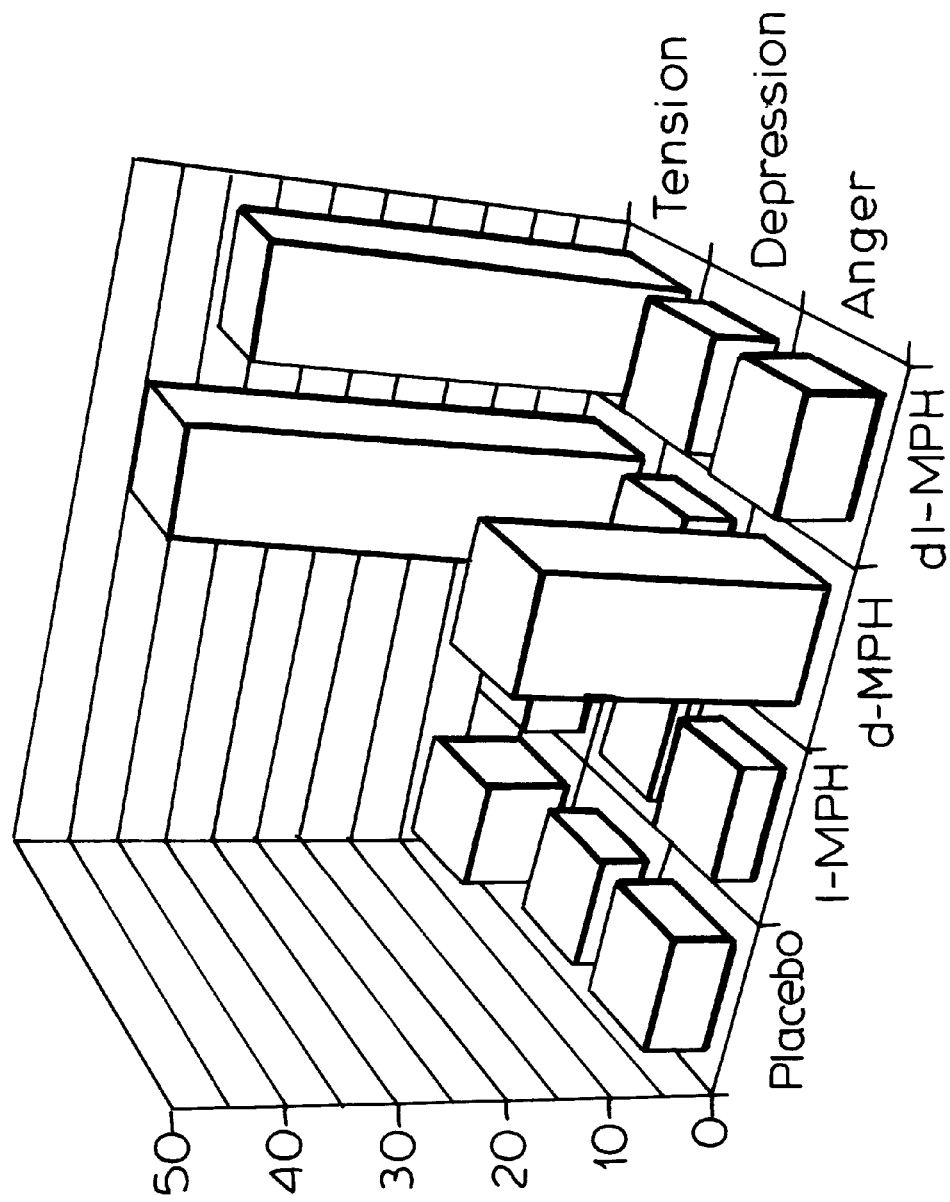
FIG. 4 is a series of 12 bar graphs showing the effect of intravenous administration of dl-MPH, d-MPH, 1-MPH and a placebo on the levels of the three components of dysphoria, namely, tension, depression and anger.

FIG. 4 depicts the response of the three components of "Dysphoria" (Tension, Depression and Anger) to the four treatments. In each case the ratings were ranked in the same order, i.e. 1-MPH<placebo<dl-MPH<d-MPH. Thus it appears that the overall pharmacodynamic effect of dl-MPH may represent an interaction between the "Dysphoric" effects of d-MPH and the -mildly euphoric effects of 1-MPH. It is conceivable that the 1-MPH will emerge as euphoriant or antidepressant in subjects with higher baseline "Dysphoria" scores such as depressed patients in whom the dose of 1-MPH will have to be titrated.

When 1-MPH exerts an immediate anti-dysphoric effect, it is unlikely that it would be addicting when administered alone without the dopaminergic effects of d-MPH. Thus while dl-MPH is addicting when abused intravenously or by snorting, 1-MPH is not addicting by any route of administration.

FIG. 4 shows the response of the three components of "dysphoria."

The 1-MPH is a valuable rapidly acting antidepressant when administered by a route that avoids first pass metabolism. The 1-MPH is particularly useful in the treatment of severely depressed hospitalized patients and in depressed suicidal patients to provide immediate relief from their intense dysphoria. The 1-MPH may be given repeatedly, either as an immediate release or as a sustained-release formulation to provide relief while awaiting onset of action of conventional antidepressants which typically take 2 to 6 weeks to become effective. The 1-MPH will help severely depressed patients to recover a sufficiently euthymic mood to restore feelings of hope and instill a new will to live.

A second use for the 1-MPH is in a diagnostic test to ascertain how responsive a patient may be to certain forms of antidepressant therapy. Patients who respond dramatically to non-orally administered 1-MPH may be patients with diminished serotonin transmission and a strongly lateralized serotonin system. A positive response to 1-MPH would suggest that treatment with a drug such as a selective serotonin re-uptake inhibitor (SSRI) such as fluoxetine hydrochloride, venlafaxine hydrochloride, paroxetine hydrochloride, nefazodone hydrochloride, and sertraline hydrochloride, would enhance serotonin transmission. While SSRLs are effective in many patients, some 30% of patients do not respond and less than half respond completely. Thus a positive response to 1-MPH is a valuable indicator that the patient is an SSRI responder and that it is worth persisting with an SSRI during the weeks it takes for this class of drugs to become effective.

Pharmacokinetics of d- and l-threo-Methylphenidate

The absolute bioavailability of 1-MPH after oral administration of the racemic drug was previously been shown to be extremely low (F–0.05) whereas that of the d=isomer was F=0.25 (2). After intravenous administration of dl-MPH, however, initial plasma concentrations of the two isomers were comparable (d:1=1:1) and there was no significant distortion in the plasma d:1 ratio until 90 minutes post dose. Total plasma clearance of 1-MPH was significantly different (higher) than that of the d-antipode after intravenous administration. The half-life, mean residence time and volume of distribution at steady state of 1-MPH were also significantly different (lower) than those of d-MPH (Table 2). There was however no significant difference between the isomers in renal clearance.

A recent positron emission topography (PET) study showed that both enantiomers of MPH were taken up into the brain after intravenous injection in baboons. [$^{11}$C]d-MPH was concentrated in the basal ganglia and cerebellum whereas the central uptake of [$^{11}$C]1-MPH was mostly non-specific (3). It has also been demonstrated that d-MPH was very effective in blocking central dopamine transporters after oral administration of d1MPH in humans (8). Data from our studies suggests that 1-MPH may have important euthymic properties in depressed patients with high baseline levels of dysphoria.

Table 2. Means (±SD) pharmacokinetic parameters for d-MPH and 1-MPH in plasma after intravenous administration of 10 mg d1-MPH in 11 healthy male volunteers.

TABLE 2

Means (±SD) pharmacokinetic parameters for d-MPH and 1-MPH in plasma after intravenous administration of 10 mg d1-MPH in 11 healthy male volunteers[a]

| | d-MPH | 1-MPH |
| --- | --- | --- |
| CL (L/kg · h$^{-1}$) | 0.04 ± 0.12 | 0.73 ± 0.028[h] |
| CL$_R$ (l/kg · h$^{-1}$) | 0.005 ± 0.003 | 0.005 ± 0.003[c] |
| MRT (h) | 6.53 ± 1.62 | 2.44 ± 0.51[b] |
| Vdss (L/kg) | 2.65 ± 1.11 | 1.80 ± 0.91[b] |
| AUC (ng/h · mL$^{-1}$) | 147.7 ± 47.90 | 88.64 ± 13.13[b] |
| t½ | 5.96 ± 1.71 | 3.61 ± 1.12[b] |

[a]Srinivas et al (2).
[b]Paired t-test: Significantly different from the d-enantiomer (p(0.01)
[c]Paired t-test: Not significantly different from the d-enantiomer

REFEERENCES (1) N. R. Srinivas, J. W. Hubbard, D. Quinn and K. K. Midha, Clin. Pharmacol. Therap. 52, 561 to 568, 1992

(2) N. R. Srinivas, J. W. Hubbard, E. D. Korchinski and K. K. Midha, Pharm. Res. 10, 14 to 21, 1993.

(3) Y. S. Ding. J. S. Fowler, S. L. Dewey, G.-J. Wang, J. Logan, S. J. Gatley and N. Pappas, Psychopharmacology 131, 71 to 78, 1997.

(4) S. L. Satel and J. C. Nelson, J. Clin. Psychiat. 50, 241 to 249, 1989

(5) R. J. Chiarello and J. O. Cole, Arch. Gen. Psychiat, 44, 286 to 295, 1987.

(6) R. E. Emptage and T. P. Semla, Annals of Pharmacotheraphy 30, 151 to 157, 1996.

(7) A. E. Wallace, L. L. Kofoed and A. N. West, Am J. Psychiat. 152, 929 to 931, 1995.

(8) N. D. Volkow, G.-J. Wang, J. S. Fowler, S. J. Gatley, J. Logan, Y.-S Ding, R. Hitzeman and N. Pappas, Amer. J. Psychiat. 155, 1325–1331, 1998.

What is claimed is:

1. A method of treating a depressed mammal by a method without dysphoria resulting from the presence of d-threo-methylphenidate which comprises the step of administering to avoid first pass metabolism orally or non-orally to said mammal, a therapeutically effective amount of l-threo-methylphenidate having an enantiomeric purity of at least 95%, or a pharmaceutically acceptable salt thereof.

2. The method of treating depression defined in claim 1 wherein the non-oral administration is intravenous, intramuscular, subcutaneous, transdermal, intranasal, intrapulmonary or rectal administration, and wherein the oral administration is sub-lingual administration.

3. The method of treating depression defined in claim 1 wherein the mammal is a human patient.

4. The method of treating depression defined in claim 1 wherein the pharmaceutically acceptable salt is a pharmaceutically acceptable acid addition salt.

5. A method of treating depression in a patient by a method without dysphoria resulting from the presence of d-threo-methylphenidate which comprises the steps of:
(a) administering non-orally to said patient, a therapeutically effective amount of l-threo-methylphenidate having an enantiomeric purity of at least 95% or a pharmaceutically acceptable salt thereof; and
(b) administering orally to said patient, a therapeutically effective amount of a conventional anti-depressant agent in conjunction with the non-oral administration of the l-threo-methylphenidate or pharmaceutically acceptable salt thereof.

6. The method of treating depression defined in claim 5 wherein the conventional antidepressant agent is a serotonin re-uptake inhibitor or an atypical antidepressant or a tricyclic antidepressant.

7. The method of treating depression defined in claim 6 wherein the serotonin re-uptake inhibitor is selected from the group consisting of fluoxetine, fluvoxamine, paroxetine, sertraline, and venlafaxine or a pharmaceutically acceptable salt thereof.

8. The method of treating depression defined in claim 6 wherein the atypical antidepressant is nefazodone or buproprion.

9. The method of treating depression defined in claim 6 wherein the tricyclic antidepressant is amitriptyline, imipramine, doxepin, maprotiline, protriptyline, nortriptyline, desipramine, clomipramine, or trimipramine.

10. A method of diagnosing the ability of a patient suffering from depression to benefit from administration of a serotonin re-uptake inhibitor, which comprises the steps of
(a) administering to said patient a therapeutically effective amount of l-threomethylphenidate having an enantiomeric purity of at least 95%; and
(b) relating any positive response to depression from the administration of the l-threo-methylphenidate according to step (a) with the ability of the patient to benefit from treatment for depression with the serotonin re-uptake inhibitor.

11. A pharmaceutical composition for treatment of depression in a form that is suitable for only non-oral administration or for oral administration in the form of sublingual administration or administration via the buccal mucosae thereby avoiding first pass metabolism which comprises:
   (a) a therapeutically effective amount of l-threo-methylphenidate having an enantiomeric purity of at least 95%; and
   (b) a pharmaceutically acceptable inert carrier or diluent suitable for the non-oral administration of l-threo-methylphenidate or for sublingual administration or administration via the buccal mucosae.

12. The method of treating a depressed mammal defined in claim 1 wherein the l-threo-methylphenidate is enantiomerically pure.

13. The method of treating depression defined in claim 5 wherein the l-threo-methylphenidate is enantiomerically pure.

14. The method of diagnosing the ability of a patient suffering from depression to benefit from administration of a serotonin re-uptake inhibitor defined in claim 10 wherein the l-threo-methylphenidate is enantiomerically pure.

15. The pharmaceutical composition for treatment of depression defined in claim 11 wherein the l-threo-methylphenidate is enantiomerically pure.

16. A method of treating depression in a patient by a method without dysphoria resulting from the presence of d-threo-methylphenidate which comprises the steps of:
   (a) administering transdermally to said patient, a therapeutically effective amount of l-threo-methylphenidate having an enantiomeric purity of at least 95% or a pharmaceutically acceptable salt thereof; and
   (b) administering orally to said patient, a therapeutically effective amount of nefazodone in conjunction with the transdermal administration of the l-threo-methylphenidate or pharmaceutically acceptable salt thereof.

* * * * *